(12) United States Patent
Yang et al.

(10) Patent No.: US 9,612,191 B2
(45) Date of Patent: Apr. 4, 2017

(54) INSPECTION DEVICE AND INSPECTION SYSTEM FOR DISPLAY SUBSTRATE

(71) Applicants: Boe Technology Group Co., Ltd., Beijing (CN); Beijing Boe Display Technology Co., Ltd., Beijing (CN)

(72) Inventors: Yu Yang, Beijing (CN); Nanren Quan, Beijing (CN); Yaoxie Zheng, Beijing (CN); Tongju Bai, Beijing (CN); Dehua Chen, Beijing (CN)

(73) Assignees: Boe Technology Group Co., Ltd., Beijing (CN); Beijing Boe Display Technology Co., Ltd., Beijing (CN)

( * ) Notice: Subject to any disclaimer, the term of this patent is extended or adjusted under 35 U.S.C. 154(b) by 291 days.

(21) Appl. No.: 14/499,567

(22) Filed: Sep. 29, 2014

(65) Prior Publication Data

US 2015/0330891 A1 Nov. 19, 2015

(30) Foreign Application Priority Data

May 15, 2014 (CN) .......................... 2014 1 0205987

(51) Int. Cl.
*G01N 21/00* (2006.01)
*G01N 21/01* (2006.01)
(Continued)

(52) U.S. Cl.
CPC ......... *G01N 21/01* (2013.01); *G01N 21/8803* (2013.01); *G01N 21/95* (2013.01);
(Continued)

(58) Field of Classification Search
CPC .............. G01N 21/86; G01N 21/8803; G01N 21/9501; G01N 21/01; G01N 21/95;
(Continued)

(56) References Cited

U.S. PATENT DOCUMENTS 6,606,154 B1 * 8/2003 Oda .................... G01N 21/9501
356/237.5
6,822,734 B1 * 11/2004 Eidelman ........... G01N 21/8806
356/237.2
(Continued)

FOREIGN PATENT DOCUMENTS

CN 1527046 9/2004
CN 1648645 8/2005
(Continued)

OTHER PUBLICATIONS

Office action from Chinese Application No. 201410205987.0 dated Dec. 22, 2015.
(Continued)

*Primary Examiner* — Hoa Pham
(74) *Attorney, Agent, or Firm* — Calfee, Halter & Griswold LLP (57) ABSTRACT

An inspection device for a substrate includes a support member, a turning table and a first drive device. The turning table includes: a carrier pivotally mounted on a pivot shaft, the carrier having an observation aperture through its thickness direction; and positioning clamps which are mounted on the carrier and are used to retain the display substrate in the range of the observation aperture. The first drive device is in transmission connection with the pivot shaft of the carrier in order to drive the turning table to rotate around the pivot shaft. In use, an omnidirectional inspection of the display substrate can be achieved by turning the turning table. Moreover, the contact between the inspector and the display substrate can be avoided, the risk of damaging the display substrate during appearance inspection can be decreased, and therefore defects of the display substrate caused by appearance inspection can be reduced.

19 Claims, 4 Drawing Sheets

(51) Int. Cl.
*G01N 21/88* (2006.01)
*G01N 21/95* (2006.01)

(52) U.S. Cl.
CPC ............... *G01N 2021/9513* (2013.01); *G01N 2201/025* (2013.01)

(58) Field of Classification Search
CPC ... G01N 2021/9513; G01N 2021/8477; G01N 2201/025
USPC ......... 356/237.1–237.5, 239.1, 239.2, 239.8; 348/95
See application file for complete search history.

(56) References Cited

U.S. PATENT DOCUMENTS 7,738,091 B2 * 6/2010 Tsuji ................. G01N 21/8803 356/237.1
2007/0091319 A1 * 4/2007 Sonda ................. G01N 21/896 356/600
2009/0097737 A1 * 4/2009 Hashimoto ........ G01N 21/8803 382/145
2014/0055773 A1 * 2/2014 Chen ................. G01N 21/8803 356/36

FOREIGN PATENT DOCUMENTS

| CN | 203011848 | | 6/2013 |
|---|---|---|---|
| CN | 204008483 | | 12/2014 |
| JP | 2000266638 | A * | 9/2000 |
| JP | 2008-070237 | | 3/2008 |

OTHER PUBLICATIONS

Office action from Chinese Application No. 201410205987.0 filed May 6, 2016.

* cited by examiner

INSPECTION DEVICE AND INSPECTION SYSTEM FOR DISPLAY SUBSTRATE

RELATED APPLICATIONS

The present application claims the benefit of Chinese Patent Application No. 201410205987.0, filed May 15, 2014, the entire disclosure of which is incorporated herein by reference.

BACKGROUND OF THE DISCLOSURE

1. Field of the Disclosure

The present disclosure relates to the technical field of display panel, and in particular, relates to an inspection device and an inspection system for display substrate.

2. Description of the Prior Art

During the usage of the display device, users have more and more stringent requirements for the appearance quality of display panel in the display device. The problems of appearance of the display panel might cause degraded product quality or even scrapped product. Therefore, during production of the display panel, the appearance yield of the display panel needs to be inspected.

In prior art, the inspection of the display panel is performed in manual way, i.e., the inspector has to pick up the display panel needing to be inspected by hand from the production line equipment in order to perform inspection. After inspection, the display panel needs to be placed back to the production line equipment by hand.

When the appearance of the display panel has inspected in the above way, the display panel being inspected is contacted by hand several times, which prone to damage the display panel or prone to generate particles, static electricity or other negative aspects, thereby degrading the product quality of the inspected display panel.

SUMMARY OF THE DISCLOSURE

The present disclosure provides an inspection device and an inspection system for display substrate, by means of which, the contact between the inspector and the display substrate can be avoided during the inspection of the display substrate, thereby the risk of damaging the display substrate by appearance inspection can be reduced.

In order to achieve the above object, the present disclosure provides the following technical solution:

an inspection device for display substrate, which comprises:

a support member;

a turning table, the turning table comprising:

a carrier pivotally mounted on the support member by a pivot shaft; the carrier having an observation aperture (observation window) through its thickness direction;

positioning clamps mounted on the carrier in order to retain the display substrate within the range of the observation aperture;

a first drive device which is in transmission connection with the pivot shaft of the carrier in order to drive the turning table to rotate around the pivot shaft.

When the display substrate is inspected by the above mentioned inspection device for display substrate, robots need to move or place the display substrate needing to be inspected to a position corresponding to the observation aperture of the carrier, and then the positioning clamps retain the display substrate in a range corresponding to the observation aperture of the carrier. Thereafter, the robots retract; the inspector can inspect the first side face of the display substrate. After the first side of the display substrate has been inspected by the inspector, the turning table can rotate around the pivot shaft of the carrier through a certain angle by the first drive device in order to continue inspection. After the turning table has turned 180 degree, the inspector can inspect another side face opposite to the first side face of the display substrate through the observation aperture of the carrier. When inspector has finished the appearance inspection of the display substrate, the carrier of the turning table can return to its initial position under the control of the first drive device. Then, the positioning clamps can be controlled to release the retaining of the display substrate. And then the robots can pick the display substrate after inspection on the carrier of the turning table and place into subsequent equipment in the production line.

Therefore, from the above description, when the appearance of the display substrate is inspected by the inspection device, omnidirectional inspection of the display substrate can be achieved by turning the turning table, the contact between the inspector and the display substrate can be avoided, and the risk of damaging the display substrate during appearance inspection can be decreased. Furthermore, other negative effects caused to the display substrate by appearance inspection can be reduced.

Preferably, the turning table comprises two positioning clamps, the two positioning clamps when closed can retain two opposite side edges of the display substrate; the turning table further comprising a second drive device driving the positioning clamps to open and close.

Preferably, each of the positioning clamps comprises: a supporter mounted on the carrier; and a pressing plate mounted on the supporter by at least one pair of slide rails and slide grooves in sliding fit, the extension direction of the side rails is in parallel with the thickness direction of the carrier.

Preferably, the second drive device comprises cylinder, wherein the body of the cylinder is mounted on the supporter and a guiding rod is mounted on the pressing plate, or alternatively the body of the cylinder can be mounted on the pressing plate and the guiding rod can be mounted on the supporter.

Preferably, in the turning table, the two positioning clamps are mounted in the carrier in the way that the spacing between the two positioning clamps can be adjusted along direction perpendicular to the length direction of the positioning clamp.

Preferably, the two positioning clamps are mounted in the carrier in a way that the spacing between the two positioning clamps can be adjusted, specifically by:

two parallel slide rails provided on the carrier, each of the positioning clamps having two linear bearings, wherein, in each of the positioning clamps, one of the linear bearings is in sliding fit with one slide rail, and the other linear bearing is in sliding fit with the other slide rail; the turning table further comprising a third drive device driving the two positioning clamps to slide along the slide rails.

Preferably, the third drive device comprises two screw shafts in corresponding with the two positioning clamps one by one; wherein, in each corresponding pair of positioning clamp and screw shaft, the screw shaft is pivotally mounted to the carrier and is disposed in parallel with the slide rails, and the supporter of the positioning clamp is in threaded fit with the screw shaft.

Preferably, the axes of the two screw shafts coincide, and the screwing directions of the two screw shaft are opposite, the two facing ends of the two screw shaft are in transmission connection by a coupling connector, and at the end of one of the screw shafts facing away from the end of the other screw shaft is provided with a drive mechanism for driving the screw shafts.

Preferably, the carrier has a plurality of stoppers along the length direction of the screw shaft.

Preferably, the carrier is provided with a plurality of positioning holes uniformly distributed in the extension direction of the slide rails, each of the positioning clamps having a lock catch, wherein, in each of the positioning clamp, when the lock catch and the positioning hole are locked together, the positioning clamp and the carrier are locked together.

Preferably, at least one cross beam is provided within the observation aperture and between the two positioning clamps, which is used to supporting the display substrate; the length direction of the cross beam and the length direction of the positioning clamp are in parallel.

Preferably, the cross beam is a cross beam made of antistatic transparent material.

Preferably, a display substrate sensor is disposed at the center position of the cross beam.

Preferably, in each of the positioning clamps, the supporter is provided with a plurality of supporting pawls along the length direction of the positioning clamp, the pressing plate is provided with pressing pawls in correspondence with the supporting pawls one by one, and both of the supporting pawls and the pressing pawls are made of antistatic transparent material.

Preferably, the first drive device is a stepper motor mounted on the support member and the pivot shaft is in transmission connection with the stepper motor.

In another aspect, the present disclosure provides an inspection system for display substrate, comprising: a cabinet and any inspection device provided by the above technical solution.

The cabinet forms a closed space. The first sidewall of the cabinet has a display substrate picking and placing port. The picking and placing port is provided with a door which is in sliding fit with the first sidewall and is used for opening and closing the picking and placing port. The cabinet is provided with a fourth drive device therein for driving the door to open and close. The inspection device is located in the closed space formed by the cabinet.

Preferably, the cabinet forms a closed space. The first sidewall of the cabinet has a display substrate picking and placing port. The picking and placing port is provided with a door which is in sliding fit with the first sidewall and is used for opening and closing the picking and placing port. The cabinet is provided with a fourth drive device therein for driving the door to open and close. The turning table and the second drive device are located in the closed space formed by the cabinet.

Preferably, the fourth drive device is cylinder, wherein the body of the cylinder is mounted on the first sidewall and a guiding rod is mounted on the door, or alternatively the body of the cylinder is mounted on the door and the guiding rod is mounted on the first sidewall.

Preferably, the inspection system further comprises an illumination lamp located under the top wall of the cabinet.

Preferably, the door is provided with at least one robot sensor.

Preferably, the inspection system further comprises a sensor disposed in the cabinet for detecting human body position in the cabinet.

DETAILED DESCRIPTION OF THE PRESENT DISCLOSURE

The technical solution in the embodiments of the present disclosure will be described in more detail in conjunction with the attached drawings in the embodiments of the present disclosure. Obviously, the described embodiments are only some of the embodiments of the present disclosure, nor all embodiments. Based on the embodiments of the present disclosure, all other embodiments made by those skilled in the art without creative work are within the protection scope of the present disclosure.

The present disclosure provides an inspection device and an inspection system for display substrate. The above mentioned display substrate can be array substrate, color film substrate and display panel etc.

Figure 1:
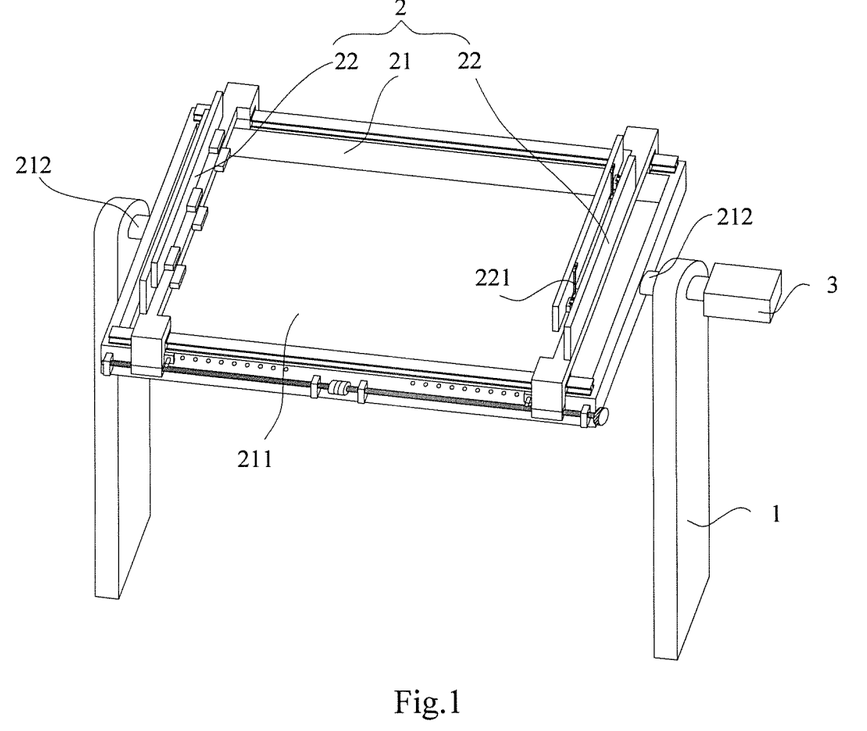
FIG. 1 is a schematic view showing the structure of the inspection device according to an embodiment of the present disclosure.
Figure 2:
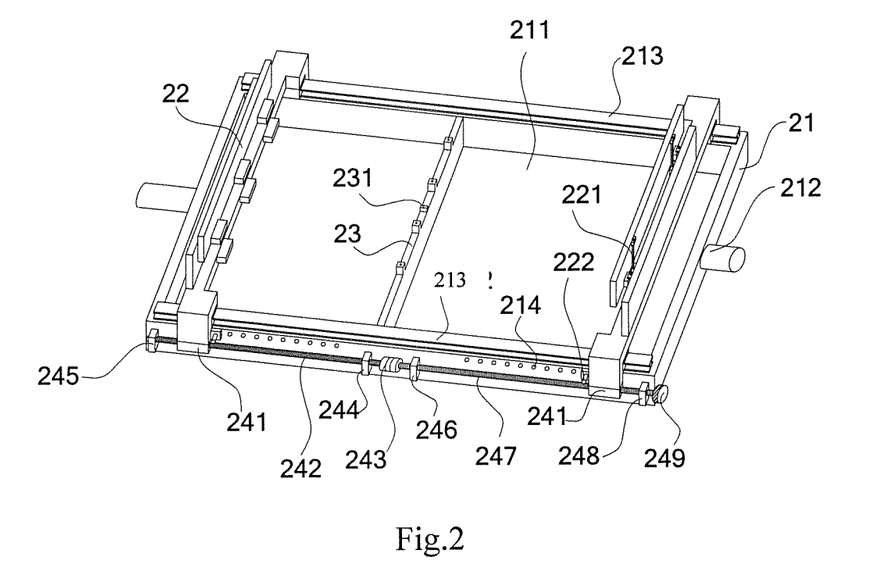
FIG. 2 is a schematic view showing the structure of the turning table in the inspection device according to an embodiment of the present disclosure.

Please refer to FIG. 1 and FIG. 2. FIG. 1 is a schematic view showing the structure of the inspection device provided by an embodiment of the present disclosure; FIG. 2 is a schematic view showing the structure of the turning table in the inspection device provided by an embodiment of the present disclosure.

As shown in FIG. 1 and FIG. 2, the inspection device for display substrate according to an embodiment of the present disclosure comprises a support member 1, a turning table 2 and a first drive device 3 which is used to drive the turning table 2 to turn relative to the support member.

As shown in FIG. 2, the turning table 2 comprises: a carrier 21 pivotally mounted on the support member 1 through a pivot shaft 212, the carrier 21 having an observation aperture 211 through its thickness direction; positioning clamps 22 mounted on the carrier 21 which are used to retain the display substrate within the range of the observation aperture 211, wherein, the first drive device 3 is in transmission connection with the pivot shaft 212 of the carrier 21 in order to drive the turning table 2 to rotate around the pivot shaft 212 of the carrier 21.

Figure 3:
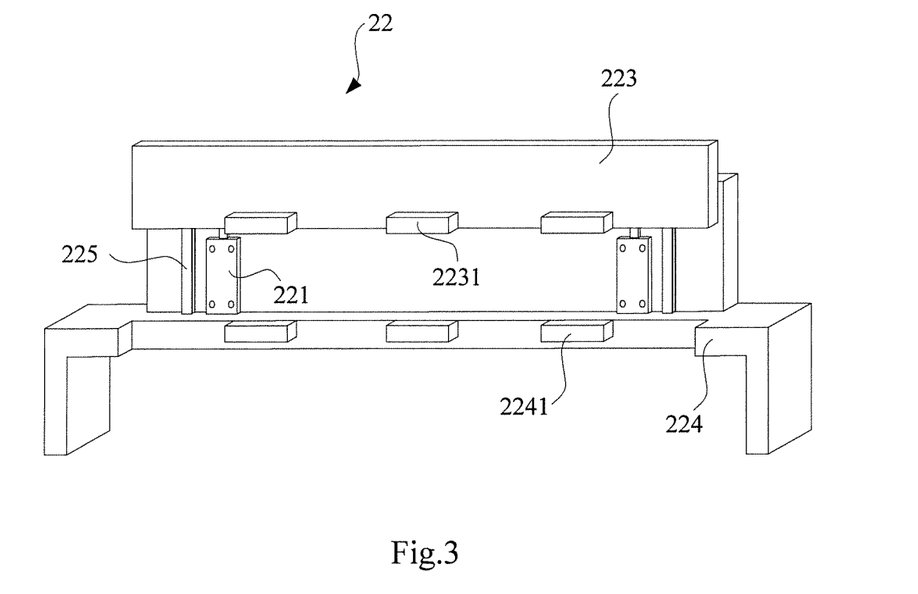
FIG. 3 is a structural schematic view of a positioning clamp of the structure of the turning table in FIG. 2.
Figure 4:
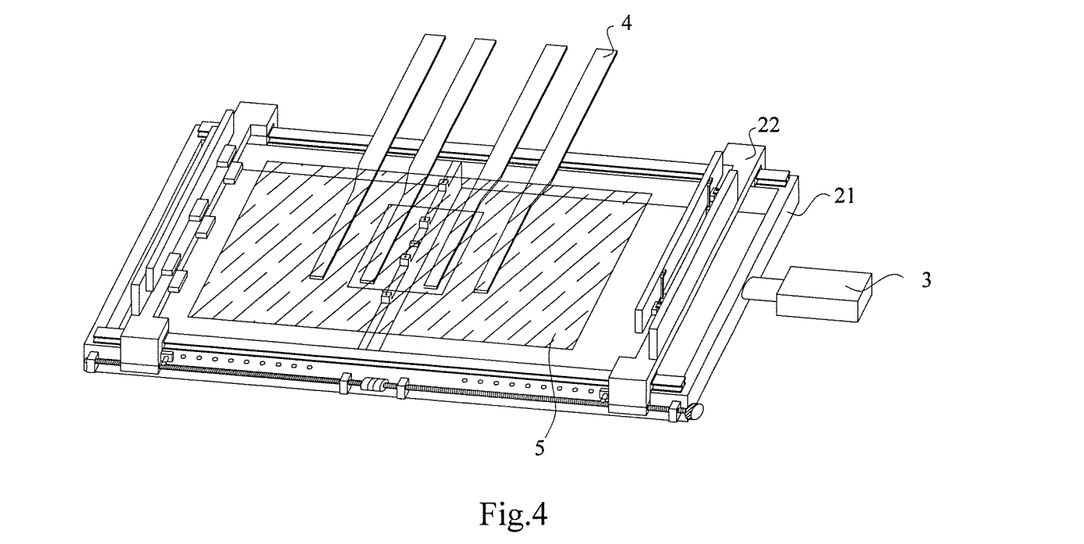
FIG. 4 is a schematic view showing the structure of the robots which are picking and placing display substrate from/onto the turning table.

Please refer to FIG. 3 and FIG. 4. FIG. 3 is a schematic view showing the structure of the positioning clamp in the structure of the turning table shown in FIG. 2; FIG. 4 is a schematic view showing the structure of the robots which are used to pick and place the display substrate from/onto the turning table.

When the appearance of the display substrate is inspected by the above mentioned inspection device for display substrate, in an operation, the robots 4 move the display substrate 5 needing to be inspected to an area opposite to the observation aperture 211 of the carrier 21; then the positioning clamps 22 retain the display substrate 5 within the range corresponding to the observation aperture 211 of the carrier 21; thereafter, the robots 4 retract and the inspector inspects the first side face of the display substrate 5. After the inspector has inspected the first side face of the display substrate 5, the display substrate will be continued to be inspected after the carrier 21 of the turning table 2 rotating around its pivot shaft 212 through a certain angle under the control of the first drive device 3, and when the carrier 21 has turned 180 degrees, the inspector can inspect the opposite side face of the display substrate 5 through the observation aperture 211 in the carrier 21. After the inspector has finished the appearance inspection of the display substrate 5, the carrier 21 of the turning table 2 returns to its initial position under the control of the first drive device 3, then the retaining of the display substrate 5 by the positioning clamp 22 is released, and the display substrate 5 is picked and placed into subsequent equipment of the production line from the carrier 21 of the turning table 2 by the robots 4.

Therefore, from the above description, when the appearance of the display substrate is inspected by the above mentioned inspection device, the contact between the inspector and the display substrate can be avoided and the risk of damaging the appearance of the display substrate during inspection can be decreased. Furthermore, any defects of the display substrate caused by appearance inspection can be reduced.

Referring to FIG. 2 and FIG. 3, in the inspection device provided by an embodiment, the turning table 2 comprises two positioning clamps 22 which can retain and clamp two side edges of the display substrate 5 when closed; the above mentioned turning table 2 further comprises a second drive device 221 which is used to drive the positioning clamp 22 to open and close.

Referring to FIG. 2 and FIG. 3, in the inspection device provided in an embodiment, each of the positioning clamps 22 comprises a supporter 224 mounted on the carrier 21; and a pressing plate 223 mounted on the supporter 224 through at least one pair of slide rails 225 and slide grooves in sliding fit. The extension direction of the slide rails 225 is in parallel with the thickness direction of the carrier 21.

The relative position between the supporter 224 and the pressing plate 223 can be adjusted in order to achieve the adjusting of closing and opening of the positioning clamp 22. The clamp and retaining of the display substrate can be realized when the supporter 224 and the pressing plate 223 are closed; the clamp and retaining of the display substrate can be released when the supporter 224 and the pressing plate 223 are open.

Referring to FIG. 3, in the inspection device provided in an embodiment, the above mentioned second drive device 221 comprises an cylinder, wherein the body of the cylinder is mounted on the supporter 224, and the guiding rod is mounted on the pressing plate 223, or alternatively, the body of the cylinder can be mounted on the pressing plate 223 and the guiding rod can be mounted on the supporter 224.

In an embodiment, the above mentioned slide rail 225 is provided on the supporter 224. A slide groove formed at the pressing plate 223 is in sliding fit with the slide rail 225. Preferably, the above mentioned slide rail 225 has an I-shaped steel structure.

In the inspection device provided in an embodiment, in the turning table 2, the two positioning clamps 22 are mounted on the carrier 21 in a way that the spacing between the two positioning clamps 22 can be adjusted along a direction perpendicular to the length direction of the positioning clamps 22. By adjusting the spacing between the two positioning clamps 22, the above mentioned inspection device can be adapted to display substrates with various dimensions, thereby to extend the application scope of the above mentioned inspection device.

Referring to FIG. 2, in a specific embodiment, the above mentioned positioning clamps 22 can be mounted on the carrier 21 in a way that the spacing between the positioning clamps 22 can be adjusted, specifically by: two slide rails 213 parallel to each other are provided on the carrier 21, each of the positioning clamps 22 is provided with two linear bearings, wherein, in each of the positioning clamps 22, one linear bearing is in sliding fit with one slide rail 213, while the other linear bearing is in sliding fit with the other slide rail 213; the turning table 2 further comprises a third drive device which is used to drive the two positioning clamps along the slide rails. Preferably, the above mentioned slide rail 213 has I-shaped steel structure.

The linear bearing can be configured to reduce the friction force when the positioning clamp 22 is sliding along the slide rails 213 and can enhance the stability of the sliding fit between the positioning clamps 22 and the slide rails 213.

More preferably, continuing to refer to FIG. 2, the above mentioned third drive device comprises two screw shafts corresponding to the two positioning clamps 22 one by one, for example, screw shaft 242 and screw shaft 247; wherein the screw shaft 242 and the screw shaft 247 are pivotally mounted on the carrier 21. The screw shaft 242 and the screw shaft 247 are parallel to the slide rails 213. The supporter 224 of one positioning clamp 22 is in threaded fitting with the screw shaft 242, and the supporter 224 of the other positioning clamp 22 is in threaded fitting with the screw shaft 247.

When the screw shaft 242 and the screw shaft 247 are driven to rotate, the positioning clamps 22 can be driven to move along the length direction of their slide rails 213, thereby the spacing between the two positioning clamps 22 can be adjusted. By adopting screw shafts for driving, the stability when driving the two positioning clamps 22 can be enhanced.

Specifically, the supporter 224 of each positioning clamp 22 is fixed with a slider 241 which is in threaded fitting with the screw shaft.

More specifically, as shown in FIG. 2, the axes of the screw shaft 242 and the screw shaft 247 coincide. The screwing direction of the screw shaft 242 is opposite to that of the screw shaft 247. The end of the screw shaft 242 facing towards the screw shaft 247 and the end of the screw shaft 247 facing towards the screw shaft 242 are in transmission connection through a coupling connector 243. The end of the screw shaft 247 away from the screw shaft 242 is provided with a drive mechanism 249 which is used to drive the screw shaft 247 and the screw shaft 242 to rotate.

The drive mechanism 249 can be a drive handle, or a drive motor, or a threaded knob etc., as long as it can be used to drive the screw shaft 242 and the screw shaft 247 to rotate, which will not be described in detail herein.

In a preferred embodiment, the carrier 21 has a plurality of stoppers 244, 245, 246, 248 distributed along the length direction of the screw shaft 242 and the screw shaft 247.

FIG. 2 specifically shows a stopper 245, a stopper 244, a stopper 246 and a stopper 248, wherein, the positioning clamp 22 in thread fitting with the screw shaft 242 can only move within the range defined by the stopper 245 and the stopper 244; meanwhile, the positioning clamp 22 in thread fitting with the screw shaft 247 can only move within the range defined by the stopper 246 and the stopper 248.

Continuing to refer to FIG. 2, in an embodiment, the carrier 21 has a plurality of positioning holes 214 evenly distributed along the extension direction of the slide rails 213. Each of the positioning clamps 22 is provided with a lock catch 222. In each of the positioning clamps 22, when the lock catch 222 is locked with one positioning hole 214 of the carrier 21, the positioning clamp 22 and the carrier 21 can be locked, thereby to improve the stability between the positioning clamp 22 and the carrier 21.

Continuing to refer to FIG. 2, in an inspection device provided in an embodiment, in order to improve the stability of the positioning of the display substrate with larger dimension by the turning table 2, the turning table 2 of the inspection device also comprises at least one cross beam 23 located in the observation aperture 211 and between the two positioning clamps 22 to support the display substrate. The length direction of the cross beam 23 is in parallel with the length direction of the positioning clamps 22.

Preferably, the above mentioned cross beam 23 is made of an antistatic transparent material.

Continuing to refer to FIG. 2, preferably, the above mentioned cross beam 23 is provided with a display substrate sensor 231 in its central position, which is used to detect whether the display substrate is present on the turning table 2.

Please referring to FIG. 3, in an inspection device provided by an embodiment, in each of the positioning clamps 22, the supporter 224 is provided with a plurality of supporting pawls 2241 evenly distributed along the length direction of the positioning clamp 22. The pressing plate 223 is provided with a plurality of pressing pawls 2231 in correspondence with the plurality of supporting pawls 2241 one by one. Both of the supporting pawls 2241 and the pressing pawls 2231 are made of antistatic transparent material. The display substrate can be positioned by the cooperation between the plurality pairs of the supporting pawls 2241 and the pressing pawls 2231, which can reduce the covering area on the display substrate by the positioning clamps 22, and is convenient to inspect the display substrate. Moreover, the antistatic transparent material can prevent the turning table 2 from causing the display substrate any electrostatic defects; meanwhile it also can enable the observer to inspect the display substrate through the supporting pawls 2241 and the pressing pawl 2231.

Based on the above various embodiments and their implementations, in the inspection device, the second drive device 221 is a stepper motor mounted at the support member 1. The pivot shaft 212 of the carrier 21 is in transmission connection with the output shaft of the stepper motor.

Figure 5:
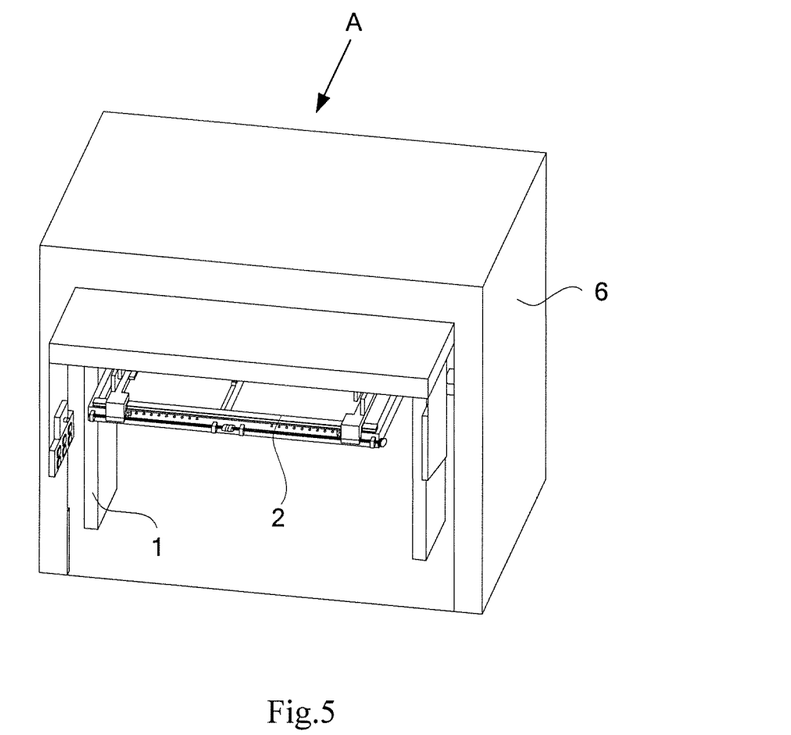
FIG. 5 is a schematic view showing the structure of the inspection system according to another embodiment of the present disclosure.
Figure 6:
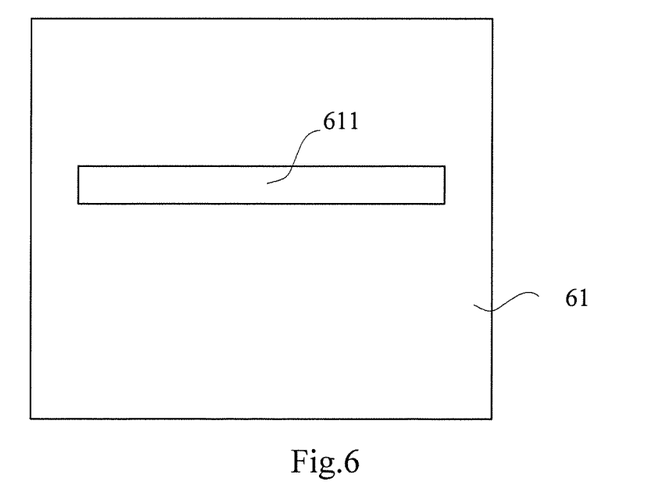
FIG. 6 is a schematic view showing the structure viewed in A direction of FIG. 5.
Figure 7:
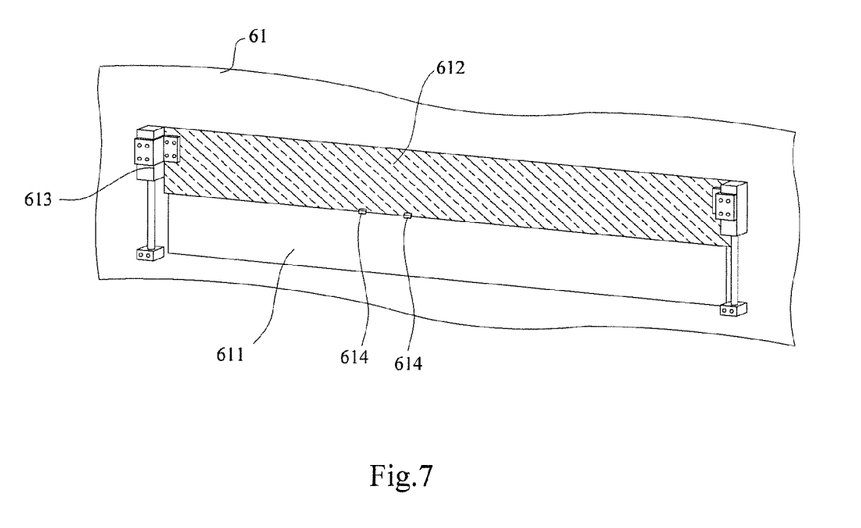
FIG. 7 is a schematic view showing the structure of the door provided in the first sidewall of the inspection system according to an embodiment of the present disclosure.

Referring to FIG. 5, FIG. 6 and FIG. 7, in order to realize closed inspection of the display substrate, the present disclosure also provides an inspection system for display substrate, comprising a cabinet 6 and an inspection device provided by the above various embodiments and their implementations.

The cabinet 6 forms a closed space. The first sidewall 61 of the cabinet 6 has a display substrate picking and placing port 611, and the picking and placing port 611 is provided with a door 612 in sliding fit with the first sidewall 61 to open and close the picking and placing port 611. A fourth drive device 613 is provided in the cabinet 6 to drive the door 612 to open and close. The above mentioned inspection device is located in the closed space formed by the cabinet 6.

When the robots are needed to place the display substrate into the interior of the cabinet 6 or pick the display substrate from the interior of the cabinet 6 after inspection, the fourth drive device 612 can drive the door 612 to open the picking and placing port 611 so that the robots can extend into the cabinet 6 through the picking and placing port 611 to operate. When the display substrate has been inspected, the fourth drive device 613 can drive the door 612 to close the picking and placing port 612 to make the cabinet 6 form a closed space, so as to make a fully closed inspection of the display substrate.

In a preferred embodiment, the fourth drive device 613 is a cylinder. The body of the cylinder is mounted on the first sidewall 61, and the guiding rod is mounted on the door 612, or alternatively, the body of the cylinder can be mounted on the door 612, and the guiding rod can be mounted on the first sidewall 61.

In an embodiment, the above mentioned inspection system also comprises an illumination lamp under the top wall of the cabinet 6. The illumination lamp can provide a light source for the closed space formed by the cabinet 6 and can provide different brightness as desired for the closed space formed by the cabinet 6 by controlling the illuminating brightness of the illumination lamp so as to inspect the appearance of the display substrate conveniently.

Referring to FIG. 7, in an embodiment, in the above mentioned inspection system, the door 612 of the cabinet 6 is provided with at least one robot sensor 614 which can detect whether the robots retract from the closed space formed by the cabinet 6. The above mentioned inspection system can ensure that the door is controlled to close the picking and placing port 611 only after the robots have retracted from the closed space of the cabinet 6, so as to avoid incorrect operation.

Of course, the number of the robot sensors 614 provided on the door 612 can be plurality, and the plurality of robot sensors 614 can have various specifications so as to detect different robots with different dimensions and specifications, which will not be described in more detail.

In an embodiment, the above inspection system also comprises a sensor in the cabinet 6 used to detect the human body position within the cabinet 6. By detecting whether human body is present in the turning space of the turning table 2, whether the turning table 2 can safely turn or not can then be determined, thereby the safety of the inspection operation can be improved.

Obviously, those skilled in the art can make various modifications and variations without departing from the spirit and scope of the present disclosure. In this way, if those modifications and variations are within the scope of the claims of the present disclosure and its equivalents, the present disclosure is meant to include those modifications and variations.

The invention claimed is:

1. A display substrate inspection device, comprising:
a support member;
a turning table, the turning table comprising:
   a carrier pivotally mounted on the support member by a pivot shaft; the carrier having an observation aperture through its thickness direction;
   two positioning clamps mounted on the carrier in order to retain a display substrate within the range of the observation aperture, wherein the position clamps retain two opposite side edges of the display substrate when the position clamps are closed;

a first drive device which is in transmission connection with the pivot shaft of the carrier in order to drive the turning table to rotate around the pivot shaft; and at least one cross beam provided within the observation aperture and between the two positioning clamps, the cross beam supporting the display substrate, wherein a length direction of the cross beam is parallel to a length direction of the positioning clamps.

2. The inspection device according to claim 1, wherein the turning table comprises a second drive device driving the positioning clamps to open and close.

3. The inspection device according to claim 2, wherein each of the positioning clamps comprises: a supporter mounted on the carrier; and a pressing plate mounted on the supporter by at least one pair of slide rails and slide grooves in sliding fit, the extension direction of the side rails is in parallel with the thickness direction of the carrier.

4. The inspection device according to claim 3, wherein the second drive device comprises a cylinder, wherein the body of the cylinder is mounted on the supporter and a guiding rod is mounted on the pressing plate, or alternatively the body of the cylinder is mounted on the pressing plate and the guiding rod is mounted on the supporter.

5. The inspection device according to claim 2, wherein in the turning table the two positioning clamps are mounted on the carrier such that the spacing of the two positioning clamps can be adjusted along a direction perpendicular to a length direction of the positioning clamps.

6. The inspection device according to claim 5, wherein the two positioning clamps are mounted on the carrier such that the spacing between the two positioning clamps can be adjusted, specifically by:

two parallel slide rails being provided on the carrier, each slide rail having an extension direction, and each of the positioning clamps having two linear bearings, wherein, in each of the positioning clamp, one of the linear bearings is in sliding fit with one slide rail, and the other linear bearing is in sliding fit with the other slide rail; the turning table further comprises a third drive device driving the two positioning clamps to slide along the slide rails.

7. The inspection device according to claim 6, wherein the third drive device comprises two screw shafts, each screw shaft having a first end, a second end, a length direction and an axis, in corresponding with the two positioning clamps one by one;

wherein, in each corresponding pair of positioning clamp and screw shaft, the screw shaft is pivotally mounted to the carrier and is disposed in parallel with the slide rails, and the supporter of the positioning clamp is in threaded fit with the screw shaft.

8. The inspection device according to claim 7, wherein the axes of the two screw shaft coincide, and the screwing directions of the two screw shaft are opposite to each other, the first end of each screw shaft facing the positioning clamp, the second ends of the two screw shafts are in transmission connection by a coupling connector, and a drive mechanism is connected to the first end of one of the screw shafts for driving the screw shafts to rotate.

9. The inspection device according to claim 8, wherein the carrier has a plurality of stoppers along the length direction of the screw shafts.

10. The inspection device according to claim 6, wherein the carrier is provided with a plurality of positioning holes uniformly distributed in the extension direction of the slide rails, each of the positioning clamps having a lock catch, wherein, in each of the positioning clamps, when the lock catch and the positioning hole are locked together, the positioning clamp and the carrier are locked together.

11. The inspection device according to claim 2, wherein in each of the positioning clamps, the supporter is provided with a plurality of supporting pawls along the length direction of the positioning clamp, the pressing plate is provided with pressing pawls in correspondence with the supporting pawls one by one, and both of the supporting pawls and the pressing pawls are made of antistatic transparent material.

12. The inspection device according to claim 1, wherein the cross beam is made of antistatic transparent material.

13. The inspection device according to claim 12, wherein a display substrate sensor is disposed at a center position of the cross beam.

14. The inspection device according to claim 1, wherein the first drive device is a stepper motor mounted on the support member and the pivot shaft is in transmission connection with an output shaft of the stepper motor.

15. An inspection system for display substrate, comprising a cabinet and an inspection device according to claim 1, wherein the cabinet forms a closed space, having side walls and a top wall, a first sidewall of the cabinet has a display substrate picking and placing port, the picking and placing port is provided with a door which is in sliding fit with the first sidewall and is used to open and close the picking and placing port, the cabinet is provided with a driving device therein for driving the door to open and close, the inspection device is located in the closed space formed by the cabinet.

16. The inspection system according to claim 15, wherein the driving device is a cylinder, wherein the body of the cylinder is mounted on the first sidewall and a guiding rod is mounted on the door, or the body of the cylinder is mounted on the door and the guiding rod is mounted on the first sidewall.

17. The inspection system according to claim 15, further comprising an illumination lamp located under the top wall of the cabinet.

18. The inspection system according to claim 15, wherein the door is provided with at least one robot sensor.

19. The inspection system according to claim 15, further comprising a sensor disposed in the cabinet for detecting human body position in the cabinet.

* * * * *